US012728177B2

(12) United States Patent
Hoffman et al.

(10) Patent No.: US 12,728,177 B2
(45) Date of Patent: Sep. 8, 2026

(54) DISINFECTANT COMPOSITION WITH RAPID ANTIVIRAL EFFICACY

(71) Applicant: Kimberly-Clark Worldwide, Inc., Neenah, WI (US)

(72) Inventors: Douglas R. Hoffman, Neenah, WI (US); Amy L. Vanden Heuvel, Neenah, WI (US); Jeremy D. Paulsen, Neenah, WI (US); Paige N. Anunson, Neenah, WI (US); Lisa M. Kroll, Neenah, WI (US); Corey T. Cunningham, Neenah, WI (US); David W. Koenig, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 469 days.

(21) Appl. No.: 18/309,329

(22) Filed: Apr. 28, 2023

(65) Prior Publication Data

US 2023/0277704 A1 Sep. 7, 2023

Related U.S. Application Data

(63) Continuation of application No. 15/744,107, filed as application No. PCT/US2015/042214 on Jul. 27, 2015, now abandoned.

(51) Int. Cl.

| | |
|---|---|
| ***A61L 2/18*** | (2026.01) |
| ***A61K 31/194*** | (2006.01) |
| ***A61K 31/205*** | (2006.01) |
| ***A61K 31/661*** | (2006.01) |
| ***A61K 45/06*** | (2006.01) |
| ***A61P 31/12*** | (2006.01) |

(52) U.S. Cl.

CPC .............. *A61L 2/18* (2013.01); *A61K 31/194* (2013.01); *A61K 31/205* (2013.01); *A61K 31/661* (2013.01); *A61K 45/06* (2013.01); *A61P 31/12* (2018.01); *Y02A 50/30* (2018.01)

(58) Field of Classification Search

CPC ...................................................... A61P 31/00

See application file for complete search history.

(56) References Cited

U.S. PATENT DOCUMENTS

| | | | |
|---|---|---|---|
| 3,494,821 | A | 2/1970 | Evans |
| 3,954,960 | A | 5/1976 | Valan |
| 4,100,324 | A | 7/1978 | Anderson et al. |
| 4,144,370 | A | 3/1979 | Boulton |
| 4,223,009 | A | 9/1980 | Chakrabarti |
| 4,445,521 | A | 5/1984 | Grollier et al. |
| 4,719,235 | A | 1/1988 | Kern |
| 4,828,912 | A | 5/1989 | Hossain et al. |
| 5,057,361 | A | 10/1991 | Sayovitz et al. |
| 5,240,764 | A | 8/1993 | Haid et al. |
| 5,284,703 | A | 2/1994 | Everhart et al. |
| 5,350,624 | A | 9/1994 | Georger et al. |
| 5,785,179 | A | 7/1998 | Buczwinski et al. |
| 5,964,351 | A | 10/1999 | Zander |
| 5,965,514 | A | 10/1999 | Wierenga et al. |
| 6,030,331 | A | 2/2000 | Zander |
| 6,158,614 | A | 12/2000 | Haines et al. |
| 6,269,969 | B1 | 8/2001 | Huang et al. |
| 6,269,970 | B1 | 8/2001 | Huang et al. |
| 6,273,359 | B1 | 8/2001 | Newman |
| 6,315,864 | B2 | 11/2001 | Anderson et al. |
| 6,403,113 | B1 | 6/2002 | Corzani |
| 6,838,078 | B2 | 1/2005 | Wang et al. |
| 6,841,527 | B2 | 1/2005 | Mitra et al. |
| 7,598,214 | B2 | 10/2009 | Cusack et al. |
| 8,034,844 | B2 | 10/2011 | Fox et al. |
| 8,105,999 | B2 | 1/2012 | Cusack et al. |
| 8,119,115 | B2 | 2/2012 | Snyder et al. |
| 8,198,326 | B2 | 6/2012 | Scholz |
| 8,337,872 | B2 | 12/2012 | Fuls et al. |
| 8,343,523 | B2 | 1/2013 | Toreki et al. |
| 8,450,378 | B2 | 5/2013 | Snyder et al. |
| 8,512,273 | B2 | 8/2013 | Rantala et al. |

(Continued)

FOREIGN PATENT DOCUMENTS

| | | |
|---|---|---|
| EP | 0 853 941 A2 | 7/1998 |
| EP | 1 531 671 B1 | 10/2013 |

(Continued)

OTHER PUBLICATIONS

Millipore Sigma (SDS: Sulfosuccinic acid; revision date: Apr. 13, 2015). (Year: 2015).*

Information on Copolymer Series INCI Name: VP/Dimethylaminoethyl Methacrylate Copolymer from Ashland, Inc. dated May 27, 2015, 2 pages.

Milipore Sigma, SDS: Sulfosuccinic acid; revision date; Apr. 13, 2015. (Year: 2015).

Sagripanti et al., "Virus Inactivation by Copper or Iron lions Alone and in the Presences of Peroxyde," Applied and Environmental Microbiology, vol. 59, No. 12, Dec. 1, 1993, pp. 4374-4376, XP002789743.

Search Report and Written Opinion for PCT/US2015/042214 dated Sep. 23, 2016, 14 pages.

(Continued)

*Primary Examiner* — Genevieve S Alley

(74) *Attorney, Agent, or Firm* — Dority & Manning, P.A.

(57) ABSTRACT

A disinfectant composition that contains a unique combination of a primary antiviral agent and a secondary antiviral agent is provided. More particularly, the primary antiviral agent includes a polyprotic acid having a low first acid dissociation constant and the secondary antiviral agent is selected from the group consisting of an anionic N-acyl compound, metal halide salt, amine compound, amine compound, aliphatic amine oxide, alkyl glycoside, alcohol ethoxylate, and combinations thereof. By selectively controlling the particular nature of each antiviral agent and their relative concentration, the present inventors have discovered that a synergistic affect can be achieved in which the disinfectant composition is capable of exhibiting an antiviral efficacy against non-enveloped viruses.

12 Claims, No Drawings

(56) References Cited

U.S. PATENT DOCUMENTS 8,673,835 B2 3/2014 Cusack et al.
9,028,852 B2 5/2015 Scholz
9,232,790 B2 1/2016 Moen et al.
9,321,803 B2 4/2016 Jiang et al.
9,629,361 B2 4/2017 Macinga et al.
9,826,770 B2 11/2017 Scholz et al.
2005/0232895 A1* 10/2005 Chen ........................ A61P 11/02 424/78.1
2006/0193745 A1 8/2006 Arndt et al.
2007/0166344 A1 7/2007 Qu et al.
2008/0045491 A1 2/2008 Fitchmun
2008/0145390 A1 6/2008 Taylor et al.
2008/0199535 A1 8/2008 Taylor et al.
2010/0255121 A1 10/2010 Perry
2012/0171155 A1 7/2012 Cunningham
2012/0171267 A1 7/2012 Cunningham et al.
2012/0171300 A1 7/2012 Koenig et al.
2012/0171301 A1 7/2012 Koenig et al.
2013/0071488 A1 3/2013 Suekuni et al.
2014/0076344 A1 3/2014 Doi et al.
2014/0369953 A1 12/2014 Purschwitz et al.
2020/0359662 A1 11/2020 Chen et al.

FOREIGN PATENT DOCUMENTS

EP 2 774 481 A1 9/2014
EP 2 807 925 A1 12/2014
GB 1 331 819 9/1973
WO WO 00/27271 A2 5/2000
WO WO 01/28337 A2 4/2001
WO WO 01/29315 A1 4/2001
WO WO 2006/062845 A2 6/2006
WO WO 2006/062857 A2 6/2006
WO WO 2012/084863 A1 6/2012
WO WO 2014/158761 A1 10/2014
WO WO 2017/019009 A1 2/2017

OTHER PUBLICATIONS

Supplementary European Search Report for EP15899807, dated Mar. 15, 2019, 11 pages.

* cited by examiner

DISINFECTANT COMPOSITION WITH RAPID ANTIVIRAL EFFICACY

CROSS REFERENCE TO RELATED APPLICATIONS

This application is a Continuation of U.S. application Ser. No. 15/744,107, filed Jan. 12, 2018, which claims priority to PCT/US2015/042214 having a filing date of Jul. 27, 2015, which is incorporated herein in its entirety by reference thereto.

BACKGROUND OF THE INVENTION

Pathogenic viruses are generally classified into two general types: enveloped and non-enveloped viruses. Some well-known enveloped viruses include herpes virus, influenza virus; paramyxovirus, respiratory syncytial virus, HIV, hepatitis B virus, hepatitis C virus, and togavirus. Non-enveloped viruses, sometimes referred to as "naked" virus include the families Picomaviridae, Reovavindae, Caliciviridae, Papovavindae, Adenoviridae and Parvoviridae. Members of these families include rhinovirus, poliovirus, adenovirus, hepatitis A virus, norovirus, coxsackievirus, enterovirus, papillomavirus, and rotavirus. "Enveloped" viruses are relatively sensitive and, thus, can be inactivated by commonly used disinfectants. In contrast, "non-enveloped" viruses are substantially more resistant to conventional disinfectants and are more environmentally stable than enveloped viruses. Thus, most disinfectants have insufficient efficacy against these types of non-envelopesd viruses. As such, a need currently exists for a disinfectant composition that is capable of exhibiting improved antiviral efficacy, particularly against non-enveloped viruses.

SUMMARY OF THE INVENTION

In accordance with one embodiment of the present invention, a disinfectant composition is disclosed that comprises from about 0.1 wt. % to about 10 wt. % of a primary antiviral agent, wherein the primary antiviral agent includes a polyprotic acid having a first acid dissociation constant of about 3.0 or less; from about 0.1 wt. % to about 15 wt. % of a secondary antiviral agent, wherein the secondary antiviral agent is selected from the group consisting of anionic N-acyl, compounds, metal halide salts, amine compounds, aliphatic amine oxides, alkyl glycosides, alcohol ethoxylates, and combinations thereof; and from about 70 wt. % to about 99.5 wt. % of a solvent system that includes one or more solvents, wherein water constitutes at least about 50 wt. % of the solvent system. The composition has a pH of about 4.5 or less and exhibits a reduction in virus infectivity of about 30% or more after being exposed to a non-enveloped virus for 10 minutes.

Other features and aspects of the present invention are discussed in greater detail below.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a disinfectant composition that contains a unique combination of a primary antiviral agent and a secondary antiviral agent. More particularly, the primary antiviral agent includes a polyprotic acid having a low first acid dissociation constant (pKas), such as about 3.0 or less, in some embodiments about 2.5 or less, and in some embodiments, from about −2.0 to about 2.4, as determined at a temperature of 25° C. The secondary antiviral agent is selected from the group consisting of an anionic N-acyl compound, metal halide salt, amine compound, aliphatic amine oxide, alkyl glycoside, and combinations thereof.

By selectively controlling the particular nature of each antiviral agent and their relative concentration, the present inventors have discovered that a synergistic effect can be achieved in which the disinfectant composition is capable of exhibiting antiviral efficacy against non-enveloped viruses, including members of the families Picornaviridae, Reoviridae, Caliciviridae, Papoviridae, Adenoviridae and Parvoviridae. Members of these families include rhinovirus, poliovirus, adenovirus, hepatitis A virus, norovirus, coxsackie, enterovirus, papillomavirus, and rotavirus. For example, after being exposed to a non-enveloped virus for only 10 minutes, the disinfectant composition can exhibit a reduction in virus infectivity of about 30% or more, in some embodiments about 50% or more, in some embodiments about 70% or more, and in some embodiments, from about 75 to about 99%, such as determined according to the test methods described herein. In one embodiment, for instance, the disinfectant composition may exhibit a reduction after only 10 minutes within the ranges noted above against Phi X174 (ATCC 13706-81), a non-enveloped bacteriophage. In another embodiment, the disinfectant composition may exhibit a reduction after only 10 minutes within the ranges noted above against feline calicivirus. Of course, the composition is also capable of inactivating other microorganisms, such as gram-negative and gram-positive bacteria, fungi, parasites, enveloped viruses, etc.

Various embodiments of the present invention will now be described in more detail below.

I. Disinfectant Composition

A. Primary Antiviral Agent

The primary antiviral agent employed in the disinfectant composition includes one or more acids having a low $pk_{a1}$ value of about 3.0 or less, in some embodiments about 2.5 or less, and in some embodiments, from about −2.0 to about 2.4, as determined at a temperature of 25° C. The acid is also polyprotic in the sense that it contains more than one mole of ionizable hydronium ions per mole of acid. The acid may likewise be organic or inorganic in nature. Specific examples of suitable polyprotic acids that have a low first dissociation constant include, for instance, organic acids, such as carboxylic acids (e.g., maleic acid ($pk_{a1}$ of 1.9) and/or sulfosuccinic acid ($pk_{a1}$ of −1.65)); inorganic acids, such as phosphoric acid ($pk_{a1}$ of 2:18); or combinations of the foregoing. Regardless of the particular type of acid employed, the primary antiviral agent, which may include one or more acids having the desired $pk_{a1}$ value, typically constitutes from about 0.1 wt. % to about 10 wt. %, in some embodiments from about 0.5 to about 8 wt. %, and in some embodiments, from about 0.8 wt. % to about 1.5 wt. % of the disinfectant composition.

B. Secondary Antiviral Agent

The secondary antiviral agent typically constitutes from about 0.1 wt. % to about 15 wt. %, in some embodiments from about 0.2 to about 10 wt. %, and in some embodiments, from about 0.5 to about 5 wt. % of the composition. As noted above, the secondary antiviral agent is selected from the group consisting of an anionic N-acyl compound, metal halide salt, amine compound, aliphatic amine oxide, alkyl glycoside, alcohol ethoxylate, as well as combinations thereof. The exact selection of the agent depends in part on the type of acid(s) employed for the primary antiviral agent. For example, the present inventors have discovered that anionic N-acyl compounds, metal halide salts, and amine compounds work particularly well with phosphoric acid. Likewise, anionic N-acyl compounds, metal halide salts, alcohol ethoxylates, aliphatic amine oxides, and alkyl glycosides work particularly well with maleic acid. Anionic N-acyl compounds and metal halide salts also work particularly well with sulfosuccinic acid.

Various specific examples of such secondary antiviral agents are described in more detail below.

Anionic N-Acyl Compounds

Anionic N-acyl compounds employed in the disinfectant composition typically have the following general structure:

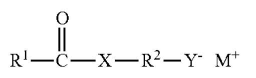

wherein, $R^1$ is a $C_4$ to $C_{40}$ fatty acid chain, in some embodiments a $C_6$ to $C_{24}$ fatty acid chain, and in some embodiments, a $C_8$ to $C_{22}$ fatty acid chain;

$R_2$ is an alkylene (e.g., methylene, dimethylene, etc.), which may optionally be substituted with alkyl, alkoxyl, alkenyl, aryl, aralkyl, alkaryl, or heterocyclyl, and which may optionally be interrupted at one or more positions by an oxygen atom;

X is O or $NR^3$, $R^3$ is H or a $C_1$ to $C_8$ alkyl (e.g., $CH_3$);

Y is $SO_3$ or $CO_2$, and

M is a cation, such as an alkali metal (e.g., sodium, potassium, etc.), alkaline earth metal (e.g., calcium, magnesium, etc.), an ammonium cation (e.g., ammonium, isopropylammonium, etc.), and so forth.

In certain embodiments, for instance, Y may be $CO_2$ and X may be $NR_3$ such that the surfactant is considered an N-acyl sarcosinate. Suitable sarcosinates may include, for example, sodium lauroyl sarconsinate, sodium myristoyl sarconsinate, potassium myristoyl sarconsinate, sodium cocoyl sarconsinate, sodium olecyl sarconsinate, triethanolamine lauroyl sarcosinate, ammonium oleoyl sarconsinate, etc. In other embodiments, Y may be $SO_3$ and X may be O such that the compound is considered an N-acyl isethionate. Suitable isethionates may include, for instance, sodium lauroyl isethionate, sodium lauroyl isethionate, sodium myristoyl isethionate, sodium cocoyl isethionate, sodium oleoyl isethionate, ammonium oleoyl isethionate, etc. In yet other embodiments, Y may be $SO_3$ and X may be $NR_3$ such that the compound is considered an N-acyl laurate. In one particular embodiment; for example, an N-acyl laurate may be employed that has the following general structure:

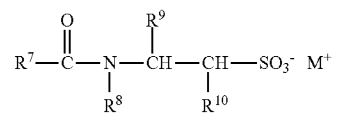

wherein, $R^7$ is a $C_8$ to $C_{30}$ fatty acid chain, in some embodiments a $C_{10}$ to $C_{24}$ fatty acid chain, and in some embodiments, a $C_{16}$ to $C_{22}$ fatty acid chain;

$R^8$ is H or a $C_1$ to $C_8$ alkyl (e.g., $CH_3$);

$R^8$ and $R^{30}$ are each independently H or a $C_1$ to $C_8$ alkyl (e.g., $CH_3$); and $M^4$ is a cation as defined above.

Particularly suitable N-acyl taurates include, for instance, sodium methyl lauroyl taurate ($R^7$ is a $C_{12}$ fatty acid chain, $R^8$ is $CH_3$, $R^3$ and $R^{30}$ are H, and M is Na), sodium methyl myristoyl taurate ($R^7$ is a $C_{12}$ fatty acid chain, $R^8$ is $CH_3$, $R^9$ and $R^{10}$ are H, and M is Na), potassium methyl myristoyl laurate ($R^7$ is a $C_{14}$ fatty acid chain, $R^8$ is $CH_3$, $R^9$ and $R^{10}$ are H, and M is K), sodium methyl cocoyl taurate ($R^7$ is a $C_{11-17}$ fatty acid chain, $R^8$ is $CH_3$, $R^8$ are H, and M is Na), sodium methyl oleoyl laurate ($R^7$ is a $C_{18}$ fatty acid chain, $R^8$ is $CH_3$, $R^9$ and $R^{10}$ are H, and M is Na), calcium methyl oleoyl taurate ($R^7$ is a $C_{18}$ fatty acid chain, $R^8$ is $CH_3$, $R^8$ and $R^{10}$ are H, and M is Ca), potassium methyl oleoyl laurate ($R^7$ is a $C_{18}$ fatty acid chain, $R^9$ is $CH_3$, $R^8$ and $R^{18}$ are H, and M is K), and ammonium methyl oleoyl taurate ($R^7$ is a $C_{18}$ fatty acid chain, $R^8$ is $CH_3$, $R^8$ and $R^{10}$ are H, and M is $NH_4$). Sodium methyl oleoyl taurate is particularly suitable for use in the present invention.

ii. Metal Halide Salts

A metal halide salt may also be employed as a secondary antiviral agent in the disinfectant composition of the present invention. More specifically, the present inventors have discovered that metal halide salts that contain a metal cation having an oxidation state of +2 or greater (e.g., +2 or +3) are particularly effective for use in the present invention. The cation may, for instance, be an alkaline earth metal, such as calcium, magnesium, etc.; transition metal, such as copper, aluminum, iron, zinc, etc.; or a combination thereof. Examples of suitable metal halide salts may include, for instance, iron (II) chloride; iron (III) chloride; zinc chloride; copper (II) chloride; aluminum (III) chloride; aluminum chlorohydrates having the formula, $Al_nCl_{(3n-m)}(OH)_m$, wherein n and m are independently from 1 to 5 (e.g., n is 2 and m is 3); etc., as well as combinations thereof.

iii. Amine Compounds

In addition to the aforementioned components, an amine compound may also be employed as the secondary antiviral agent, which typically has the following general structure:

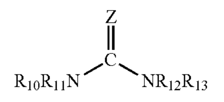

wherein,

Z is O, NH, or $NH_2^+Q^-$, wherein Q is an anion, such as a halogen (e.g., chlorine, fluorine, etc.);

$R_{10}$, $R_{11}$, $R_{12}$, and $R_{13}$ are independently hydrogen, hydroxyl, carboxyl, alkyl (e.g., $CH_3$), carboxyalkyl, or $NR_{14}R_{15}$, wherein $R_{14}$ and $R_{15}$ are independently H or alkyl.

In certain embodiments, for example, Z may be O. Examples of such compounds include, for instance, urea ($R_{10}$, $R_{11}$, $R_{12}$, and $R_{13}$ are hydrogen) and urea derivatives, such as hydroxyurea ($R_{10}$, $R_{11}$, $R_{12}$, are hydrogen and $R_{13}$ is OH), and so forth. In other embodiments, Z may be NH. Examples of such compounds include, for instance, guanidine ($R_{10}$, $R_{11}$, $R_{12}$, and $R_{13}$ are hydrogen) and guanidine derivatives, such as creatine ($R_{10}$ and $R_{11}$ are hydrogen, $R_{12}$, 1*s* $CH_3$, and $R_{13}$ is carboxymethyl ($CH_2C(O)OH$). In yet other embodiments, Z may be $NH_2^+$. Examples of such compounds include, for instance, guanidine hydrochloride ($R_{10}$, $R_{11}$, $R_{12}$, and $R_{13}$, are hydrogen and Q is Cl) and aminoguanidine hydrochloride ($R_{13}$ is $NR_{14}R_{15}$, $R_{10}$, $R_{11}$, $R_{12}$, $R_{14}$, $R_{15}$ are hydrogen and Q is Cl).

iv. Aliphatic Amine Oxides

An aliphatic amine oxide may also be employed as a secondary antiviral agent in the disinfectant composition, Typically, such aliphatic amine oxides having the following general structure:

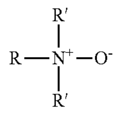

wherein,

R is an alkyl, alkenyl, or alkylamido group having from 8 to 28 carbon atoms, and in some embodiments, from 10 to 24 groups: and R' are each independently hydrogen or a $C_1$-$C_4$ alkyl group (e.g., $CH_3$).

In certain embodiments, for example, R is an alkyl group. Particular examples of such alkyl amine oxides include, for instance, decylamine oxide (each R' is $CH_3$ and R is $(CH_2)_9CH_3$); behenamine oxide (each R' is $CH_3$ and R is $(CH_2)_{21}CH_3$); lauramine oxide (each R' is $CH_3$ and R is $(CH_2)_{11}CH_3$), etc. In other embodiments, for example, R is an alkylamido group such that the resulting amine oxide is considered an alkylamido amine oxide. Particular examples of such alkylamido amine oxides include, for instance, lauramidopropylamine oxide (each R' is $CH_3$ and R is $(CH_2)_3NHC(O)(CH_2)_{10}CH_3$); palmitamidopropylamine oxide (each R' is $CH_3$ and R is $(CH_2)_3NHC(O)(CH_2)_{14}CH_3$); isostearamidopropylamine oxide (each R' is H and R is $(CH_2)_3NHC(O)(CH_2)_{16}CH_3$), etc.

v. Alkyl Glycosides

Alkyl glycosides are broadly defined as condensation products of long chain alcohols and a saccharide and are generally represented by the formula, $(Z)_n$—O—R, wherein Z is a saccharide residue, n is from 1 to about 1000, and R is an alkyl group. The saccharide residue "Z" of the alkyl glycoside typically has at least 3 carbon atoms, and in some embodiments, from 3 to 20 carbon atoms, and in some embodiments from 4 to 6 carbon atoms. The saccharide residue may, for instance, be a residue of glucose, fructose, maltose, maltotriose, lactose, galactose, mannose, dextrose, xylose, sucrose, leucrose, and so forth. Glucose is particularly suitable. The designation "n" represents the average number of saccharide residues in a particular sample of alkyl glycoside. For example, the alkyl glycoside may be a monosaccharide (n=1), disaccharide (n=2), trisaccharide (n=3), oligosaccharide (n=4 to 20), or polysaccharide (n>20). In most embodiments, "n" is 1. The "alkyl group" of the alkyl glycoside is generally a linear alkyl group (i.e., a straight chain alcohol residue). More specially, the present inventors have discovered that certain alkyl groups are particularly effective against viruses. Namely, the alkyl glycoside desirably includes alkyl groups having 4 to 12 carbon atoms, and in some embodiments, from 6 to 10 carbon atoms. Examples of such alkyl glycosides include, for instance, decyl glucoside, octyl glucoside, lauryl glucoside, etc.

vi. Alcohol Ethoxylates

Alcohol ethoxylates can also be used as a secondary antiviral agent. Such ethoxylates generally have the structure, R—O—$(CH_2CH_2O)_nH$, where R is an alkyl group having from 6 to 28 carbon atoms, in some embodiments from 8 to 22 carbon atoms, and in some embodiments, from 10 to 16 carbon atoms, and n is from 2 to 60, in some embodiments from 3 to 40, and in some embodiments, from 3 to 15. Some examples of suitable alcohol ethoxylates may include, for instance, $C_{11-15}$ pareth-3 (R is $CH_3CH(CH_2)_mCH_3$, m is from 8 to 12, and n is 3); $C_{11-15}$ pareth-12 (R is $CH_3CH(CH_2)_mCH_3$, m is from 8 to 12, and n is 12); laureth-9 (R is $(CH_2)_{11}CH_3$ and n is 9), etc. Polymeric and oligomeric alcohol ethoxylates may also be employed that contain a monomeric substructure with the formula above. One example of such an oligomeric alcohol ethoxylate is, for instance, a polyethylene glycol-modified hydrogenated triglyceride, such as PEG-100 hydrogenated castor oil.

C. Solvent System

A solvent system containing one or more solvents is also typically employed in the disinfectant composition. The solvent system may, for instance, constitute from about 70 wt % to about 99.5 wt. %, in some embodiments from about 80 wt. % to about 99 wt. %, and in some embodiments, from about 85 wt. % to about 98 wt. % of the composition. Suitable solvents may include, for instance, water, glycols (e.g., ethylene glycol, propylene glycol, butylene glycol, triethylene glycol, hexylene glycol, polyethylene glycols, ethoxydiglycol, dipropyleneglycol, etc.); glycol ethers (e.g., methyl glycol ether; ethyl glycol ether, isopropyl glycol ether, etc.); alcohols (e.g., methanol, ethanol, n-propanol, iso-propanol, and butanol): ketones (e.g., acetone, methyl ethyl ketone, and methyl isobutyl ketone); esters (e.g., ethyl acetate, butyl acetate, diethylene glycol ether acetate, methoxypropyl acetate, ethylene carbonate, propylene carbonate, etc.); amides (e.g., dimethylformamide, dimethylacetamide dimethylcaprylic/capric fatty acid amide and N-alkylpyrrolidones); sulfoxides or sulfones (e.g., dimethyl sulfoxide (DMSO) and sulfolane); and so forth.

While a wide variety of solvents may be employed, one beneficial aspect of the present invention is that can exhibit good antiviral efficacy without the need for alcohol-based solvents (e.g., ethanol) often employed in conventional disinfectant compositions. In fact, the disinfectant composition of the present invention may be generally free of such alcohol-based solvents (e.g., ethanol). When employed, for instance, alcohol-based solvents typica y constitute no more than about 5 wt. %, in some embodiments no more than about 3 wt %, and in some embodiments, from 0 wt. % to about 1 wt. % of the disinfectant composition. Furthermore, water is typically the primary solvent such that the composition is considered "aqueous." In most embodiments, for example, water constitutes at least about 50 wt. %, in some embodiments at least about 75 wt. %, and in some embodiments, from about 90 wt. % to 100 wt. % of the solvent system.

D. Cationic Surfactant

Although by no means required, the disinfectant composition may, in some cases, contain one or more cationic surfactants to further enhance the overall antimicrobial activity. When employed, such cationic surfactants may constitute from about 0.1 wt. % to about 15 wt. %, in some embodiments from about 0.2 to about 10 wt. %, and in some embodiments, from about 0.5 to about 5 wt. % of the composition. Examples of suitable cationic surfactants may include, for instance, biguanides and bisbiguanides (e.g., chlorhexidine, guanide, etc.), quaternary ammonium salts (e.g., benzalkonium chloride and alkyl substituted derivatives, cetylpyridinium halides, benzethonium chloride, etc. Quaternary ammonium salts, for instance, may be particularly useful in disinfectant composition of the present invention. Such salts typically contain one quaternary ammonium group attached to at least one $C_6$-$C_{18}$ linear or branched alkyl or aralkyl chain. Particularly suitable compounds of this class may be represented by the following formula:

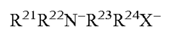
$R^{21}R^{22}N^-R^{23}R^{24}X^-$ wherein,

- $R^{21}$ and $R^{22}$ are $C_1$-$C_{18}$ linear or branched alkyl, alkenyl, or arylalkyl chains that may be substituted in available positions by N, O, or S, provided at least one $R^{21}$ or $R^{22}$ is a $C_8$-$C_{18}$ linear or branched alkyl, alkenyl, or arylalkyl chains that may be substituted in available positions by N, O, or S;
- $R^{23}$ and $R^{24}$ are $C_1$-$C_6$ alkyl, phenyl, benzyl, or $C_8$-$C_{12}$ arylalkyl groups, or $R^{23}$ and $R^{24}$ may also form a ring (e.g., pyridine ring) with the nitrogen of the quaternary ammonium group; and
- $X^-$ is an anion, such as a halide (e.g., fluoride, chloride, bromide, iodide, and most desirably, chloride), carboxylate, carbonate, bicarbonate, sulfate (e.g., methosulfate, ethosulfate, etc.), and so forth.

Examples of such compounds include, benzalkonium halides having an alkyl chain length of $C_{12}$-$C_{16}$, benzalkonium ha ides substituted with alkyl groups on the phenyl ring, dimethyldialkylammonium halides in which the alkyl groups have chain lengths of $C_6$-$C_{16}$; benzethonium halides and alkyl substituted benzethonium halides, and so forth.

E. Other Components

In addition to those noted above, a variety of other components may also be incorporated into the disinfectant composition of the present invention, such as chelators, nonionic surfactants, anionic surfactants, zwitterionic surfactants, propellants, pH adjustors (e.g., sodium hydroxide), fragrances, colorants, preservatives, chaotropic agents, antioxidants, light stabilizers, film-forming polymers, etc. In certain embodiments, for instance, one or more film-forming polymers may be employed to help the composition form a film on a hard surface. One example of such a polymer is a vinylpyrrolidone copolymer having the following formula:

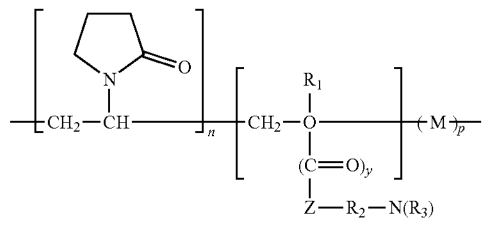

wherein,

- n is from 20 to 99, and in some embodiments, from 40 to 90,
- m is from 1 to 80, and in some embodiment, from 5 to 40;
- p is from 0 to 50, and in some embodiments, from 5 to 20, and wherein the tolal of n+m+p is typically 100;
- $R_5$ is H or a or $C_1$ to $C_4$ alkyl (e.g., $CH_3$);
- Z is O, S, or NH, and in some embodiments, O;
- $R_2$ is $(CH_2)_x$;
- x is from 1 to 18, and in some embodiments, from 2 to 10;
- y is 0 or 1;
- $R_3$ is independently hydrogen or a $C_1$ to $C_4$ alkyl (e.g., $CH_3$); and
- M is a vinyl or vinylidene monomer copolymerizable with vinyl pyrrolidone.

The monomer unit $[\ ]_m$ is, lor example, a di-lower alkylamine alkyl (meth)acrylate or a vinyl ether derivative. Examples of these monomers include, for instance, dimethylaminomethyl acrylate, dimethylaminomethyl methacrylate, diethylaminomethyl acrylate, diethylaminomethyl methacrylate, dimethylaminoethyl acrylate, dimethylaminoethyl methacrylate, dimethylaminobutyl acrylate, dimethylaminobutyl methacrylate, dimethylaminoamyl methacrylate, diethylaminoamyl methacrylate, dimethylaminohexyl acrylate, diethylaminohexyl methacrylate, dimethylaminocctyi acrylate, dimethylaminooctyl methacrylate, diethylaminooctyl acrylate, diethylaminooctyl methacrylate, dimethylaminodecyl methacrylate, dimethylaminododecyl methacrylate, diethylaminolauryl acrylate, diethylaminotauryl methacrylate, dimethylaminoslearyl acrylate, dimethylammostearyl methacrylate, diethylaminostearyl acrylate, diethylaminostearyl methacrylate, di-t-butylaminoethyl methacrylate, di-t-butylaminoethyl acrylate, dimethylamino vinyl ether, etc., as well as combinations thereof.

The monomer unit "M", which is optional, may include any conventional vinyl monomer copolymetizable with N-vinyl pyrrolidone. Thus, for example, suitable conventional vinyl monomers include alkyl vinyl ethers (e.g., methyl vinyl ether, ethyl vinyl ether, octyl vinyl ether, etc.); acrylic and methacrylic acid and esters thereof (e.g., methacrylate, methyl methacrylate, etc.); vinyl aromatic monomers (e.g., styrene, a-methyl styrene, etc.); vinyl acetate; vinyl alcohol; vinylidene chloride; acrylonitrile and substituted derivative thereof; methacrylonitrile and substituted derivatives thereof; acrylamide and methacrylamide and N-substituted derivatives thereof; vinyl chloride, crotonic acid and esters thereof; etc.

In certain embodiments, $R_1$ and/or $R_3$ may be methyl. Likewise, y may be 1 and/or $R_2$ may be $(CH_2)_2$ or $(CH_2)_3$. One particular example of such a polymer is a vinylpyrrolidone/dimethyl-aminoethylmethate copolymer, which has the following general structure:

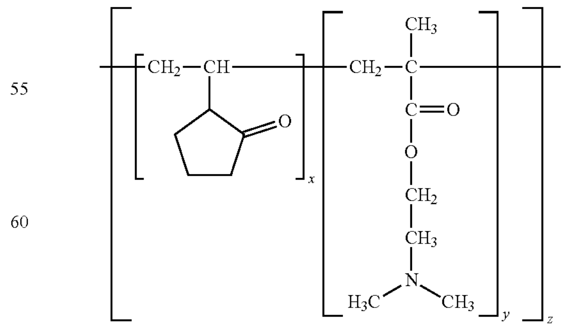

wherein x, y and z are at least 1 and have values selected such that the weight average molecular weight of the vinylpyrrolidone/dimethylamino ethylmethacrylate copolymer is from about 10,000 to about 5,000,000. Commercially available polymers of this type include Copolymer 845, Copolymer 937, and Copolymer (Ashland, Inc.). In yet another embodiments, the vinylpyrrolidine copolymer may have the following general structure:

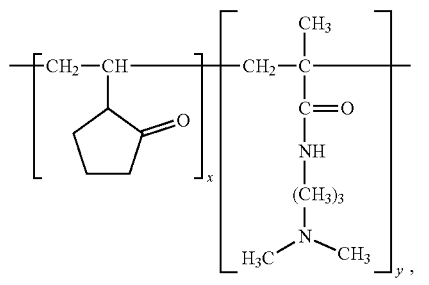

wherein x, y and z are at least 1 and have values selected such that the weight average molecular weight of the copolymer is from about 10,000 to about 5,000,000. Techniques for synthesizing such polymers are well known in the art and described in more detail U.S. Pat. Nos. 4,445,521; 4,223,009; and 3,954,960, as well as GB 1331819.

Another suitable film-forming polymer is a polyquaternary ammonium polymer that contains two or more quaternary ammonium centers within the compound structure. For instance, the polyquaternary ammonium polymer typically has the following general structure:

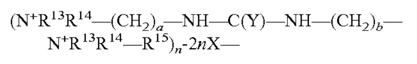

$(N^+R^{13}R^{14}—(CH_2)_a—NH—C(Y)—NH—(CH_2)_b—N^+R^{13}R^{14}—R^{15})_n\text{-}2nX—$ wherein, $R^{13}$ and $R^{14}$ are independently alkyl (e.g., methyl, ethyl, isopropyl, etc.), hydroxyalkyl (e.g., hydroxymethyl, hydroxyethyl, etc.), or $—CH_2CH_2(OCH_2CH_2)$ OH;

$R^{15}$ is a linking group and may be $(CH_2)_d$ or $\{(CH_2)_eO(CH_2)_f\}_g$;

Y is O, S or NH, and in some embodiments, O;

a, b, c, d, e and f are each independently from 1 to 6, in some embodiments from 1 to 4, and in some embodiments, from 2 to 3;

g is from 1 to 4, and in some embodiments, from 1 to 2;

n is at least 2, in some embodiments from 2 to 200, and in some embodiments, from 3 to 100; and X is an anion, such as a halide (e.g., fluoride, chloride, bromide, iodide, and most desirably, chloride), carboxylate, carbonate, bicarbonate, sulfate (e.g., methosulfate, ethosulfate, etc.), and so forth.

In certain embodiments, $R^{13}$ and/or $R^{14}$ may be methyl. Likewise, "a" may be 3 and/or "b" may be 3. $R^{15}$ may likewise be $((CH_2)_eO(CH_2)_f)_g$ and "e" may be 2, "f" may be 2, and/or "g" may be 1. In one particular embodiment, for instance, the polyquaternary ammonium polymer may be poly[bis(2-chloroethyl) ether-alt-1,3-bis[3-(dimethylamino) propyl]urea] quaternized (also known as "Polyquaternium-2" using INCI nomenclature), which has the following general structure:

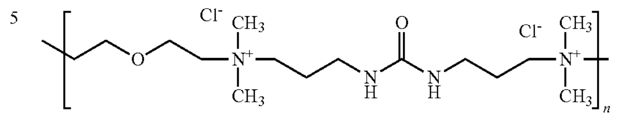

wherein n is as defined above.

If desired, the relative amount of the vinylpyrrolidone copolymer and/or polyquaternary ammonium polymer in relation to the primary antiviral agent within the composition can be controlled to improve the residual efficacy of the composition. For example, vinylpyrrolidone copolymers may be present in an amount of from about 50 to about 90 parts, in some embodiments from about 60 to about 90 parts, and in some embodiments, from about 65 to about 85 parts per 100 parts of the primary antiviral agent employed in the composition. In certain embodiments, for instance, such copolymers may constitute from about 0.2 wt. % to about 5 wt. %, in some embodiments from about 0.5 to about 3 wt. %, and in some embodiments, from about 0.6 to about 2 wt. % of the composition. Likewise, polyquaternary ammonium copolymers may be present in an amount of from about 30 to about 70 parts, in some embodiments from about 35 to about 65 parts, and in some embodiments, from about 40 to about 60 parts per 100 parts of the primary antiviral agent employed in the composition. In certain embodiments, for instance, such polymers may constitute from about 0.1 wt. % to about 3 wt. %, in some embodiments from about 0.2 to about 2 wt. %, and in some embodiments, from about 0.3 to about 1.5 wt. % of the composition. Vinylpyrrolidone copolymers are also typically employed in an amount greater than the polyquaternary ammonium polymers, and the weight ratio of vinylpyrrolidone copolymers to polyquaternary ammonium polymers may be from about 1.0 to about 8.0, in some embodiments from about 1.1 to about 5.0, and in some embodiments, from about 1.2 to about 3.0.

The composition may also contain a preservative or preservative system to inhibit the growth of microorganisms. Suitable preservatives may include, for instance, alkanols, disodium EDTA (ethylenediamine tetraacetate), EDTA salts, EDTA fatty acid conjugates, isothiazolinone, benzoic esters (parabens) (e.g., methylparaben, propylparaben, butylparaben, ethylparaben, isopropylparaben, isobutylparaben, benzylparaben, sodium methylparaben, and sodium propylparaben), benzoic acid, propylene glycols, sorbates, urea derivatives (e.g., diazolindinyl urea), and so forth. Other suitable preservatives include those sold by Ashland, Inc., such as "Germall 115" (amidazolidinyl urea), "Germall II" (diazolidinyl urea), and "Germall Plus" (diazolidinyl urea and iodopropyl butylcarbonate). Another suitable preservative is Kathon CG®, which is a mixture of methylchlorohiazolinone and methylisothiazolinone available from Dow Chemical; Mackstat H 66 (available from Solvay). Still another suitable preservative system is a combination of 56% propylene glycol, 30% diazolidinyl urea, 11% methylparaben, and 3% propylparaben available under the name GERMABEN® II from Ashland, Inc. The disinfectant composition typically has a pH of about 4.5 or less, in some embodiments about 4.0 or less, and in some embodiments, from about 1.0 to about 3.5. To help achieve the desired pH level, various pH modifiers may be optionally employed. Some examples of pH modifiers that may be used in the present invention include, but are not limited to, ammonia; mono- and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia, sodium, potassium, lithium hydroxide; sodium, potassium, and lithium meta silicates; monoethanolamine; triethylamine; isopropanolamine; diethanolamine and triethanoamine. When utilized, the pH modifier may be present in any effective amount needed to achieve the desired pH level.

II. Use of the Composition

The disinfectant composition may generally be used to reduce microbial or viral populations on a wide variety of surfaces, such as a hard surface or a surface on a user/patient (e.g., skin). Exemplary hard surfaces include, for instance, lavatory fixtures, lavatory appliances (toilets, bidets, shower stalls, bathtubs, sinks, and bathing appliances), walls, flooring surfaces, surfaces associated with food preparation (e.g., tables, counters, restaurant, kitchens, sinks, etc.), surfaces associated with hospital environments, medical laboratories and medical treatment environments. The manner in which the disinfectant composition is applied to a surface can vary as desired. For example, in certain embodiments, the composition may be applied directly to the surface. In such an application, a user generally applies the composition (e.g., with a pump) and then removes the composition from the treated area after a certain period of time using a wipe. In other embodiments, however, it may be desired that the composition is first applied to a wipe prior to use. The wipe may provide an increased surface area to facilitate contact of the composition with microorganisms. In addition, the wipe may also serve other poses, such as providing water absorption, barrier properties, etc. The wipe may also eliminate microorganisms through frictional forces imparted to the surface.

The wipe may be formed from any of a variety of materials as is well known in the art. Typically, however, the wipe includes a fibrous web that contains absorbent fibers. For example, the wipe may be a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single multi-layered. Normally, the basis weight of such a paper product is less than about 120 grams per square meter ("gsm"), in some embodiments less than about 80 gsm, in some embodiments less than about 60 grams per square meter, and in some embodiments, from about 10 to about 60 gsm.

Any of a variety of materials can also be used to form the paper web(s) of the product. For example, the material used to make the paper product may include absorbent fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, bamboo, algae, and so forth. In addition, in some Instances, synthetic fibers can also be utilized.

If desired, the absorbent fibers (e.g., pulp fibers) may be integrated with synthetic fibers to form a composite. Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes, polylactic acid, polyhydroxyalkanoate; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, and/or after web formation. Other known methods for increasing wettability may also be employed, such as described in U.S. Pat. No. 5,057,361 to Sayovitz, et al. The relative percentages of such fibers may vary over a wide range; depending on the desired characteristics of the composite. For example, the composite may contain from about 1 wt. % to about 60 wt. %, in some embodiments from 5 wt. % to about 50 wt. %, and in some embodiments, from about 10 wt. % to about 40 wt. % synthetic polymeric fibers. The composite may likewise contain from about 40 wt. % to about 99 wt. %, in some embodiments from 50 wt. % to about 95 wt. %, and in some embodiments, from about 60 wt. % to about 90 wt. % absorbent fibers.

Composites, such as described above, may be formed using a variety of known techniques. For example, a nonwoven composite may be formed that is a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al. Alternatively, the nonwoven composite may be formed be formed by hydraulically entangling staple length fibers and/or filaments with high-pressure jet streams of water. Various techniques for hydraulically entangling fibers are generally are disclosed, for example, in U.S. Pat. No. 3,494,821 to Evans and U.S. Pat. No. 4,144,370 to Bouolton. Hydraulically entangled nonwoven composites of continuous filaments (e.g., spunbond web) and natural fibers (e.g., pulp) are disclosed, for example, in U.S. Pat. No. 5,284,703 to Everhart et al, and U.S. Pat. No. 6,315,864 to Anderson, et al. Hydraulically entangled nonwoven composites of staple fiber blends (e.g., polyester and rayon) and natural fibers (e.g., pulp), also known as "spunlaced" fabrics, are described, for example, in U.S. Pat. No. 5,240,764 to Haid et al.

Regardless of the materials or processes utilized to form the wipe, the basis weight of the wipe is typically from about 20 to about 200 grams per square meter ("gsm"), and in some embodiments, between about 35 to about 100 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al; U.S. Pat. No. 6,269,969 to Huang et al.; U.S. Pat. No. 6,269,970 to Huang, et al.; and U.S. Pat. No. 6,273,359 to Newman, et al.

The composition may be incorporated into the wipe during its formation or simply coated onto all or a portion of a surface of the wipe using known techniques, such as printing, dipping, spraying, melt extruding, coating (e.g., solvent coating, powder coating, brush coaling, etc.), foaming, and so forth. In one embodiment, for example, the composition is applied to the wipe by dipping, spraying, or printing. If desired, the composition may be applied in a pattern that covers from about 5% to about 95%, in some embodiments from about 10% to about 90%, and in some embodiments, from about 20% to about 75% of a surface of the wipe. Such patterned application may have various benefits, including enhanced aesthetic appeal, improved absorbency, etc. The particular type or style of the pattern is not a limiting factor of the invention, and may include, for example, any arrangement of stripes, bands, dots, or other geometric shape. The pattern may include indicia (e.g., trademarks, text, and logos), floral designs, abstract designs, any configuration of artwork, etc. It should be appreciated that the "pattern" may take on virtually any desired appearance.

If desired, the disinfectant composition may be present on the wipe in the form of a liquid such that the wipe is considered a "wet wipe." The total amount of the disinfectant composition employed in such "wet wipes" (including any solvents) depends in part upon the type of wipe material utilized, the type of container used to store the wipes, the nature of the composition, and the desired end use of the wipes. Generally, however, each wet wipe contains from about 150 wt. % to about 600 wt. %, and desirably from about 300 wt. % to about 500 wt. % of the disinfectant composition on the dry weight of the wipe.

Once applied to a surface (e.g., hard surface), solvents can evaporate from the disinfectant composition so that a film is formed. The solvent content (e.g., water content) of the resulting film may be, for instance, less than about 5 wt %, in some embodiments less than about 2 wt. %, and in some embodiments, less about 1 wt. %. In such embodiments, the film typically contains primary antiviral agents (e.g., acids) in an amount of from about 10 wt. % to about 50 wt. %, in some embodiments from about 15 wt % to about 45 wt. %, and in some embodiments, from about 20 wt. % to about 40 wt. %. The film may also contain secondary antiviral agents in an amount of from about 10 wt. % to about 50 wt. %, in some embodiments from about 15 wt. % to about 45 wt. %, and in some embodiments, from about 20 wt. % to about 40 wt %. Of course, the film may contain other components, such as film-forming polymers. For example, the film may contain vinylpyrrolidone copolymers in an amount of from about 10 wt. % to about 40 wt. %, in some embodiments from about 15 wt. % to about 35 wt. %, and in some embodiments, from about 20 wt. % to about 30 wt. %, as well as polyquaternary ammonium polymers in an amount of from about 1 wt. % to about 30 wt. %, in some embodiments from about 5 wt. % to about 25 wt. %, and in some embodiments, from about 10 wt. % to about 20 wt. %. The film may also optionally contain cationic surfactants in an amount of from about 10 wt. % to about 50 wt. %, in some embodiments from about 15 wt. % to about 45 wt. %, and in some embodiments, from about 20 wt. % to about 40 wt %. Regardless of its exact constituents, the resulting film is capable of exhibiting a residual degree of antiviral efficacy. The film is also physically stable so that it can still remain active alter being abraded multiple times. For example, after being exposed to a virus for 10 minutes, the film itself can exhibit a logo reduction of about 0.5 or more, in some embodiments about 0.8 or more, in some embodiments about 1.0 or more, and in some embodiments, from about 1.2 to about 3.0, such as determined in accordance with a residual virucidal activity test. The film can also exhibit antiviral activity after a substantial period of time on the surface, such as after 24 hours, and in some cases, even after 48 hours. In one embodiment, for instance, the film may exhibit a $\log_{10}$ reduction after 24 or 48 hours of approximately 2.0-5.0 against a feline calicivirus or murine norovirus. In another embodiment, the film may exhibit a logs reduction after 24 hours or 48 hours within the ranges noted above against Phi-X 174 (ATCC 13706-81), a non-enveloped bacteriophage.

The present invention may be better understood will reference to the following examples.

TEST METHODS

Protocol for Propagation of Bacteriophage: Phi X174

1. Tryptic soy broth (TSB) containing 0.7% w/v agar (this mixture is called top agar) was prepared. Autoclave and store at 49° C. in a water bath or dry bead/sand bath.
2. Aliquot 4 ml of top agar into sterile 14 ml test tubes.
3. Inoculate 10 top agar tubes w/ the concentrated phage stock from ATCC. Also add 100 μl of a 24 h *E. coli* ATCC 13706 host culture that has been washed 1× in Butterfields Phosphate Buffer. (For frozen ATCC phage stock, add 500 μl TSB warmed to 49° C.)
4. Dump individual top agar tubes onto individual TSA plates warmed to room temperature. Ensure top agar is spread across the entire plate surface. Allow top agar to solidify, invert plates, and incubate for 24 hours @ 37° C.

5. Plates should show complete clearing (with the exception of possible pinpoint colonies throughout).
6. Add 2 ml of warm SM buffer (Teknova) to each plate and scrape the top agar with a sterile white Teflon policeman.
7. Using a serological pipette, transfer the scrapped top agar, liquid to a 15 ml conical centrifuge lube (1 tube per plate).
8. Vortex each lube for about 10-15 secs.
9. Centrifuge the tubes at 1000×g for 25 minutes. Make sure the tubes are distributed equally on each side of the centrifuge rotor.
10. After centrifuging, combine the resulting supernatant into a new sterile 50-mL centrifuge tube.
11. Wet the filter unit with sterile beef extract and replace the 50-mL centrifuge tube for collection of bacteriophage so it remains undiluted by the beef extract.
12. Pass all the collected bacteriophage supernatant through 50-ml 0.2 μm filtration unit.
13. Dilute and plate the filtrate to determine the PFU/ml. Store the filtrate in a refrigerator.

Virucidal Infectivity:

Bacteriophage Phi X174 (ATCC 13706-81) was added 1:10 (–108 plaque forming units (PFU) per sample) into a solution containing the composition of interest. Following a 10-minute exposure, the sample was transferred 1:10 into Tryptic Soy Broth (TSB). Following 10 minutes in TSB, a second 1:10 dilution was completed into an outgrowth solution for the Phi X174 host (*E. coli* ATCC 13706) that contained TSB and a resazurin dye. *E. coli* outgrowth was then monitored at 37° C. for 16-24 hours and the rate of fluorescence development was calculated. The rate observed when Phi X174 was not exposed to any composition represented a 100% Phi X174 signal. The rate observed without Phi X174 present represented a "0% signal." The rate obtained following Phi X174 exposure to a given composition was compared to the signal obtained with no exposure to calculate the "percent reduction in virus infectivity."

EXAMPLE

Various formulations were formed as set forth in the table below. Once formed, the virus infectivity was tested according to the method described above. The results are set forth below.

| | Secondary Antiviral Agent Alone | | Secondary Antiviral Agent in Combination with Primary Antiviral Agent (% values represent reduction in virus infectivity) | | | |
|---|---|---|---|---|---|---|
| Secondary Antiviral Agent | Concentration (mM) | % Reduction | Concentration (mM) | Maleic Acid (3 mM) | Phosphonc Acid (50-150 mM) | Sulfosuccinic Acid (10-32 mM) |
| None | — | — | — | 1-8% | 0-47% | 0-75% |
| Plantacare 818 UP | 2 | 5% | 30 | 99% | 6% | 0% |
| (Cocoglucoside) | 6 | 0% | 50 | 0% | 0% | 0% |
| | 17 | 0% | 60 | 0% | 0% | 0% |
| | 51 | 0% | 80 | 0% | 0% | 0% |
| Hostapon TPHC | 25 | 0% | 25 | 0% | 99% | 99% |
| (Sodium Methyl | 42 | 0% | 42 | 0% | 96% | 88% |
| Oleoyl Taurate) | 50 | 0% | 50 | 0% | 99% | 50% |
| | 67 | 0% | 67 | 0% | 99% | 1% |
| Genaminox CHE | 30 | 0% | 30 | 0% | — | — |
| (Coco dihydroxy | 51 | 0% | 51 | 0% | — | — |
| ethyl amine oxide) | 61 | 0% | 61 | 0% | — | — |
| | 81 | 0% | 81 | 0% | — | — |
| Mackamine C-10 | 6 | 7% | 30 | 10% | 0% | 6% |
| (Decylamina oxide) | 18 | 4% | 49 | 35% | 0% | 0% |
| | 53 | 11% | 59 | 64% | 0% | 2% |
| | 183 | 30% | 79 | 62% | 0% | 0% |
| Ammonyx LMDO | 2 | 5% | 30 | 32% | 0% | 0% |
| (Lauramidopropyl- | 6 | 11% | 50 | 97% | 0% | 0% |
| amine Oxide) | 17 | 0% | 61 | 0% | 0% | 0% |
| | 50 | 0% | 81 | 0% | 0% | 0% |
| Hetoxide HC 200- | 0.2 | 12% | 0.4 | 71% | 11% | 3% |
| 50% | 0.7 | 0% | 0.7 | 0% | 0% | 0% |
| (PEG-200 | 2 | 3% | 1 | 0% | 47% | 0% |
| Hydrogenated | 6 | 15% | 3 | 0% | 26% | 0% |
| Castor Oil | | | | | | |
| EcoSense 3000 | 8 | 14% | 0.3 | 0% | — | — |
| (Decyl Glucoside) | 23 | 0% | 1 | 0% | — | — |
| | 69 | 0% | 7 | 0% | — | — |
| | 207 | 0% | 37 | 0% | — | — |
| Tergitol 15-S-3 | 6 | 0% | 0.2 | 99% | 21% | 0% |
| (C11-15 Pareth-3) | 18 | 7% | 1 | 0% | 17% | 0% |
| | 54 | 9% | 6 | 0% | 1% | 0% |
| | 161 | 4% | 29 | 0% | 2% | 0% |
| Tergitol 15-S-12 | 6 | 0% | 0.2 | 3% | — | — |
| (C11-15 Sec- | 17 | 0% | 1 | 0% | — | — |
| Pareth-12) | 50 | 0% | 6 | 0% | — | — |
| | 151 | 0% | 30 | 12% | — | — |
| Hetoxol LA-9 | 6 | 0% | 0.2 | 9% | 57% | 5% |
| (Laureth-9) | 17 | 0% | 1 | 65% | 62% | 0% |
| | 50 | 0% | 5 | 0% | 11% | 0% |
| | 150 | 2% | 27 | 0% | 10% | 0% |

-continued

| Secondary Antiviral Agent | Secondary Antiviral Agent Alone Concentration (mM) | % Reduction | Secondary Antiviral Agent in Combination with Primary Antiviral Agent (% values represent reduction in virus infectivity) Concentration (mM) | Maleic Acid (3 mM) | Phosphonc Acid (50-150 mM) | Sulfosuccinic Acid (10-32 mM) |
|---|---|---|---|---|---|---|
| Aluminum | 2 | 1% | 2-7 | 17% | 43% | 99% |
| chlorohydrate | 6 | 3% | 6-14 | 28% | 34% | 99% |
| (Aluminum | 18 | 2% | 18-27 | 9% | 29% | 99% |
| chiorohydrate) | 55 | 9% | 55 | 99% | 68% | 99% |
| iron (iii) chloride | 8 | 3% | 8 | 0% | — | 99% |
| (Ferric chloride) | 17 | 18% | 17 | 23% | — | 99% |
| | 33 | 21% | 33 | 0% | — | 99% |
| | 66 | 32% | 66 | 0% | — | 99% |
| Zinc Chloride (Zinc | 2 | 5% | 2-7 | 99% | 10% | 99% |
| Chloride) | 6 | 0% | 6-13 | 99% | 28% | 99% |
| | 18 | 0% | 18-26 | 99% | 58% | 99% |
| | 53 | 0% | 53 | 0% | 88% | 99% |
| Copper (II) Chionde | 1 | 20% | 1-3 | 72% | 44% | 94% |
| | 9 | 23% | 4-6 | 57% | 87% | 96% |
| | 4 | 18% | 11-13 | 38% | 80% | 99% |
| | 27 | 99% | 26 | 70% | 99% | 99% |
| Urea (Urea) | 7 | 0% | 3 | 8% | 57% | 1% |
| | 20 | 0% | 9 | 6% | 71% | 0% |
| | 60 | 0% | 28 | 1% | 53% | 25% |
| | 180 | 0% | 85 | 0% | 56% | 0% |
| Guanidine | 6 | 0% | 3 | 0% | 40% | 10% |
| Hydrochloride | 18 | 0% | 10 | 0% | 34% | 12% |
| (Guanidine HCl) | 55 | 0% | 29 | 0% | 34% | 1% |
| | 164 | 0% | 86 | 0% | 46% | 0% |
| Aminoguanidine | 6 | 2% | 3 | 12% | 50% | 0% |
| Hydrochloride | 18 | 7% | 9 | 4% | 86% | 0% |
| (Aminoguanidine | 53 | 4% | 28 | 0% | 50% | 4% |
| HCl) | 158 | 1% | 85 | 0% | 99% | 13% |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A disinfectant composition comprising:

from about 0.1 wt. % to about 10 wt. % of a primary antiviral agent, wherein the primary antiviral agent includes a polyprotic acid having a first acid dissociation constant of about 3.0 or less;

from about 0.1 wt. % to about 15 wt. % of a secondary antiviral agent; and from about 70 wt. % to about 99.5 wt. % of a solvent system that includes one or more solvents, wherein water constitutes at least 50 wt. % of the solvent system;

wherein the disinfectant composition has a pH of about 4.5 or less;

wherein the polyprotic acid is sulfosuccinic acid and the secondary antiviral agent is a metal halide salt.

2. The disinfectant composition of claim 1, wherein the metal halide salt is copper (II) chloride, iron (II) chloride, iron (III) chloride, zinc chloride, aluminum (III) chlonde, or aluminum chlorohydrate.

3. The disinfectant composition of claim 1, further comprising a cationic surfactant.

4. The disinfectant composition of claim 1, wherein the disinfectant composition exhibits a reduction in virus infectivity of about 30% or more after being exposed to a nonenveloped virus for 10 minutes.

5. The disinfectant composition of claim 4, wherein the disinfectant composition exhibits a reduction in virus infectivity of about 30% or more after being exposed to Phi X174 (ATCC 13706-B1) for 10 minutes.

6. The disinfectant composition of claim 1, wherein the disinfectant composition exhibits a reduction in virus infectivity of about 70% or more after being exposed to Phi X174 (ATCC 13706-B1) for 10 minutes.

7. A method for disinfecting a surface, the method comprising contacting the surface with the disinfectant composition of claim 1.

8. The method of claim 7, wherein the disinfectant composition is exposed to Phi X174 (ATCC 13706-B1) for 10 minutes, wherein the disinfectant composition exhibits a reduction in virus infectivity of about 30% or more, or 70% or more, after being exposed to Phi X174 (ATCC 13706-B1) for 10 minutes.

9. The method of claim 7, wherein the disinfectant composition is used against a non-enveloped virus selected from the families Picornaviridae, Reoviridae, Caliciviridae, Papovaviridae, Adenoviridae, Parvoviridae, and combinations thereof.

10. The method of claim 7, wherein the surface is a hard surface.

11. The method of claim 7, wherein the disinfectant composition is disposed on a wipe prior to being applied to the surface.

12. A disinfectant composition comprising:

from about 0.1 wt. % to about 10 wt. % of a primary antiviral agent, wherein the primary antiviral agent includes a polyprotic acid having a first acid dissociation constant of about 3.0 or less;

from about 0.1 wt. % to about 15 wt. % of a secondary antiviral agent; and from about 70 wt. % to about 99.5 wt. % of a solvent system that includes one or more solvents, wherein water constitutes at least 50 wt. % of the solvent system;

wherein the disinfectant composition has a pH of about 4.5 or less;

wherein the polyprotic acid is sulfosuccinic acid and the secondary antiviral agent is a metal halide salt, wherein the metal halide salt is copper (II) chloride.

* * * * *